United States Patent [19]

Gordon et al.

[11] 4,203,992

[45] May 20, 1980

[54] β-BROMOPENICILLANIC ACID SULFONE

[75] Inventors: Eric M. Gordon, Pennington; William H. Koster, Ringoes, both of N.J.

[73] Assignee: E. R. Squibb & Sons, Inc., Princeton, N.J.

[21] Appl. No.: 968,538

[22] Filed: Dec. 11, 1978

[51] Int. Cl.$^2$ .................... A61K 31/43; C07D 499/44
[52] U.S. Cl. ................... 424/271; 260/239.1; 260/245.2 R
[58] Field of Search ............... 260/307.6 C, 239.1; 424/270, 271

[56] References Cited

U.S. PATENT DOCUMENTS

| | | | |
|---|---|---|---|
| 3,197,466 | 7/1965 | Chow et al. | 260/239.1 |
| 3,741,959 | 6/1973 | Looker et al. | 260/239.1 |

FOREIGN PATENT DOCUMENTS 956605  4/1964  United Kingdom .

OTHER PUBLICATIONS

Fisher et al., Annual Reports in Med. Chem. 13, 239 (1978).
Cole, Enzyme Biotechnology, p. 222 (1978).
Clayton, J. Chem. Soc. (c) 2123 (1969).
Loosemore et al., J. Org. Chem. 43 (18) 3611 (1978).
Pratt et al., Proc. Nat'l Acad. Sci. USA, 75 (9), 4145 (1978).
English et al., Antimicrobial Agents & Chemotherapy 14 (3) 414 1978.
Sykes et al., J. of Antimic Chemotherapy 2, 115 (1976).

*Primary Examiner*—Norman Morgenstern
*Assistant Examiner*—Vera C. Clarke
*Attorney, Agent, or Firm*—Lawrence S. Levinson; Dale Lovercheck; Donald J. Barrack

[57] ABSTRACT

(2S,5R,6S)-6β-Bromo-3,3-dimethyl-7-oxo-4-thia-1-azabicyclo[3.2.0]heptane-2-carboxylic acid, S,S-dioxide, physiologically acceptable salts thereof and readily hydrolyzable ester thereof inhibit the action of the β-lactamase enzyme RTEM.

6 Claims, No Drawings

β-BROMOPENICILLANIC ACID SULFONE

BACKGROUND OF THE INVENTION

Bacteria that are normally susceptible to attack by β-lactam antibiotics can develop a resistance to such attack by the production of a β-lactamase enzyme. These enzymes catalyze the hydrolysis of the lactam ring of a β-lactam antibiotic to a β-amino acid derivative, which is not active against bacteria.

One β-lactamase enzyme is the RTEM enzyme. The RTEM enzyme is of plasmid origin and is said to be the most widely distributed β-lactamase among the enteric gram-negative bacteria; see, Fisher et al., *Annual Reports in Medicinal Chemistry*, 13:239 (1978). The RTEM enzyme is capable of transferring into bacteria that are susceptible to β-lactam antibiotics and rendering the organism resistant to these drugs; this ability to transfer from organism to organism, of course compounds the problem of the RTEM enzyme. This can be seen most clearly in the development recently of an ampicillin-resistant strain of *N. gonorrhoeae*.

Two approaches have been followed in the search for a way to overcome, or at least minimize, the effects of β-lactamases. The first is the synthesis of novel β-lactam antibiotics which are stable against β-lactamases. These efforts have enjoyed some success; however, the resistant derivatives synthesized seem to have a lower degree of antibacterial activity than the non-resistant analogs. The second approach comprises the use of a compound which inhibits the action of β-lactamase enzymes on the lactam ring of a β-lactam antibiotic. These β-lactamase inhibitors are used in conjunction with the β-lactam antibiotics.

RELATED APPLICATION

U.S. Patent application Ser. No. 968,539, filed Dec. 11, 1978, discloses that (2S,5R,6S)-6α-bromo-3,3-dimethyl-7-oxo-4-thia-1-azabicyclo[3.2.0]heptane-2-carboxylic acid, S,S-dioxide, salts thereof, and readily hydrolyzable esters thereof, are inhibitors of the β-lactamase enzyme RTEM.

BRIEF DESCRIPTION OF THE INVENTION (2S,5R,6S)-6β-Bromo-3,3-dimethyl-7-oxo-4-thia-1-azabicyclo[3.2.0]heptane-2-carboxylic acid, S,S-dioxide, salts thereof, and readily hydrolyzable esters thereof, are inhibitors of the β-lactamase enzyme RTEM. This invention is directed to the above-named novel sulfone compound, to compositions comprising at least one of the above-named compounds in combination with a β-lactam antibiotic susceptible to degradation by the RTEM enzyme, and to a method of inhibiting the action of the β-lactamase enzyme RTEM on the β-lactam antibiotic by the use of one of the above-named compounds.

DETAILED DESCRIPTION OF THE INVENTION

The novel compound of this invention, (2S,5R,6S)-6β-bromo-3,3-dimethyl-7-oxo-4-thia-1-azabicyclo[3.2.0]heptane-2-carboxylic acid, S,S-dioxide, salts thereof, and readily hydrolyzable esters thereof, can be obtained using 6,6-dibromopenicillanic acid as a starting material. 6,6-dibromopenicillanic acid is known in the art; see, for example, Clayton, *J. Chem. Soc.* (*C*), 2123 (1969).

The carboxyl group in 6,6-dibromopenicillanic acid must be protected prior to the reduction of the molecule. This can be accomplished by reaction of the acid with a bulkyl ester group. The benzhydryl group has been found to be an effective protecting group, which can be cleaved without effecting the rest of the molecule. The benzhydryl ester can be formed by reacting the acid with diphenyldiazomethane in an organic solvent, e.g., ethyl acetate.

Treatment of the benzhydryl ester of 6,6-dibromopenicillanic acid with a reducing agent, e.g., tri-n-butyl tin hydride, yields the benzhydryl ester of a 6β-bromopenicillanic acid.

Oxidation of 6β-bromopenicillanic acid, benzhydryl ester yields the corresponding sulfone. The oxidation can be accomplished using any of the methods known to be useful for oxidizing a sulfur atom. Exemplary of the oxidizing agents which can be used are meta-chloroperbenzoic acid, hydrogen peroxide, potassium permanganate, etc. The oxidation reaction can be run in an organic solvent, e.g., ethyl acetate, or in water containing a miscible organic solvent, e.g., dioxane. Reaction temperature is not critical, and the reaction is conveniently run at room temperature.

Alternative methods for the production of the products of this invention are available. For example, (2S, 5R, 6S)-6β-bromo-3,3-dimethyl-7-oxo-4-thia-1-azabicyclo [3.2.0] heptane-2-carboxylic acid, S,S-dioxide can be obtained by first cleaving the ester group from 6β-bromopenicillanic acid benzhydryl ester and then oxidizing the resulting acid.

Physiologically acceptable salts of (2S,5R,6S)-6β-bromo-3,3-dimethyl-7-oxo-4-thia-1-azabicyclo[3.2.0]-heptane-2-carboxylic acid, S,S-dioxide are readily obtained using conventional techniques and are useful as β-lactamase inhibitors. Exemplary of the salts specifically contemplated are those formed with a metal ion, e.g., alkali metal ions or alkaline earth metal ions, or amine salt ions.

Readily hydrolyzable esters of (2S,5R,6S)-6β-bromo-3,3-dimethyl-7-oxo-4-thia-1-azabicyclo-[3.2.0]heptane-2-carboxylic acid, S,S-dioxide are easily obtained using conventional techniques and are useful as β-lactamase inhibitors. Exemplary of the ester groups which are readily hydrolyzed in vivo are those having the structural formula —CH(Y)—O—CO—alkyl, wherein Y is hydrogen or alkyl, e.g., acetoxymethyl and pivaloyloxymethyl; methoxymethyl; and isobenzofuranyl.

As discussed above, under the heading "Background of the Invention", the RTEM enzyme is a β-lactamase enzyme that catalyzes the hydrolysis of the lactam ring of a β-lactam antibiotic yielding a derivative which is not active against bacteria. The treatment of a mammalian host with a β-lactam antibiotic susceptible to degradation by the RTEM enzyme can be made more effective by the administration of (2S,5R,6S)-6β-bromo-3,3-dimethyl-7-oxo-4-thia-1-azabicyclo[3.2.0]heptane-2-carboxylic acid, S,S-dioxide, or a physiologically acceptable salt thereof, or a readily hydrolyzable ester thereof, in conjunction with the antibiotic. A compound of this invention can be administered simultaneously with a β-lactam antibiotic or separately.

Compositions comprising an RTEM enzyme inhibitor of this invention and a β-lactam antibiotic susceptible to degradation by the RTEM enzyme are within the scope of this invention. The weight ratio of inhibitor to antibiotic can be from about 1:10 to 10:1, preferably from about 1:3 to 3:1. Formulation of these compositions can be accomplished using conventional techniques, e.g., in powder form for reconstitution with a sterile vehicle for injection in solution; in suspension for oral administration; or the like. The compositions will preferably be formulated for administration in the manner conventionally used for administration of the antibiotic.

Many of the known β-lactam antibiotics have been shown to be susceptible to degradation by the RTEM enzyme. Current thinking (see, for example, Sykes et al., *J. of Antimic Chemotherapy,* 2,115 (1976) is that most of the penicillin antibiotics are susceptible (although to varying degrees) to degradation by the RTEM enzyme. Exemplary penicillins are ampicillin, amoxicillin, penicillin V, penicillin G, carbenicillin and sulbenicillin. The cephalosporins are not as susceptible as the penicillins to degradation by the RTEM enzyme; cephaloridine and cephalothin are exemplary of cephalosporins that are susceptible to degradation by the RTEM enzyme.

The following example is illustrative of this invention.

EXAMPLE (2S,5R,6S)-6β-Bromo-3,3-dimethyl-7-oxo-4-thia-1-azabicyclo[3.2.0]heptane-2-carboxylic acid, S,S-dioxide (a)
(2S,5R,6S)-6,6-Dibromo-3,3-dimethyl-7-oxo-4-thia-1-azabicyclo[3.2.0]heptane-2-carboxylic acid, benzhydryl ester (2S,5R,6S)-6,6-Dibromo-3,3-dimethyl-7-oxo-4-thia-1-azabicyclo[3.2.0]heptane-2-carboxylic acid (23.24 g, 64.7 mM) is dissolved in ethyl acetate (400 ml) and a solution of diphenyldiazomethane (12.57 g, 64.7 mM) in ethyl acetate (100 ml) is added dropwise while stirring. Nitrogen evolves rapidly during addition and the reaction mixture is allowed to stand for about 16 hours at room temperature. The mixture is washed with saturated sodium bicarbonate solution, then with water, dried over sodium sulfate, and the solvent is removed in vacuo. The residual foam is solidified with ether, chromatographed on silica gel (500 g), and crystallized from ether to yield the title compound (17.13 g), melting point 128°–130° C.; IR (m.o. mull) 1800, 1745 cm$^{-1}$;

Anal. Calc'd. for $C_{21}H_{19}NO_3SBr_2$: C, 48.02; H, 3.65; N, 2.67; Br, 30.43. Found: C, 48.27; H, 3.59; N, 2.62; Br, 30.40.

(b)
(2S,5R,6S)-6β-Bromo-3,3-dimethyl-7-oxo-4-thia-1-azabicyclo[3.2.0]-heptane-2-carboxylic acid, benzhydryl ester.

To a solution of (2S,5R,6S)-6,6-dibromo-3,3-dimethyl-7-oxo-4-thia-1-azabicyclo[3.2.0]heptane-2-carboxylic acid benzhydryl ester (2 g, 3.81 mM) in dry dichloromethane (50 ml) cooled in an ice bath under a nitrogen atmosphere is added tri-n-butyl tin hydride (1.10 ml, 4.17 mM) and the mixture is stirred at 0°–5° C. for 4 hours. The mixture is allowed to stand at 12° C. for about 16 hours and the solvent is then removed in vacuo. The residual oil is chromatographed on silica gel (125 g). The desired product is eluted with dichloromethane and obtained as an oil (856 mg); IR (CHCl$_3$) 1790, 1750 cm$^{-1}$; NMR (CDCl$_3$)δ, 1.23 (S,CH$_3$), 1.62 (S,CH$_3$), 4.6 (S,H$_3$), 5.25 (d,J=4 Hz, H$_5$), 5.55 (d,J=4 Hz, H$_6$).

(c)
(2S,5R,6S)-6β-Bromo-3,3-dimethyl-7-oxo-4-thia-1-azabicyclo[3.2.0]heptane-2-carboxylic acid, S,S-dioxide benzhydryl ester.

(2S,5R,6S)-6β-Bromo-3,3-dimethyl-7-oxo-4-thia-1-azabicyclo[3.2.0]heptane-2-carboxylic acid, benzhydryl ester (456 mg, 1.02 mM) is dissolved in dichloromethane (30 ml) and 85% pure m-chloroperbenzoic acid (477 mg, 2.35 mM) is added. The mixture is stirred at room temperature for 24 hours and then washed with saturated sodium bicarbonate solution, followed by water and dried over sodium sulfate. Removal of solvent in vacuo gives an oil which is purified by preparative thin-layer chromatography (silica gel, dichloromethane) yielding the product as a foam: i.e. (CHCl$_3$) 1815, 1755 cm$^{-1}$; NMR (CD$_3$COCD$_3$)δ, 1.2 (S,CH$_3$), 1.6 (S,CH$_3$), 4.75 (S,H$_3$) 5.27 (d,J=4.5,H$_5$), 5.87 (d,J=4.5H$_6$) Anal. Calc'd for $C_{21}H_{20}NO_5SBr$: C, 52.72; H, 4.21; N, 2.93; BR, 16.71. Found: C, 52.83; H, 4.07; N, 2.70; Br, 16.43

(d) (2S, 5R, 6S)-6β-Bromo-3,3-dimethyl-7-oxo-4-thia-1-azabicyclo[3.2.0]heptane-2-carboxylic acid, S,S-dioxide To a solution of (2S,5R,6S)-6β-bromo-3,3-dimethyl-7-oxo-4-thia-1-azabicyclo[3.2.0]heptane-2-carboxylic acid, S,S-dioxide, benzhydryl ester (316 mg, 0.661 mM) and dry anisole (361 μl, 330 mM) in dry dichloromethane (5 ml) cooled to −15° C. to −20° C. under nitrogen is added anhydrous trifluoroacetic acid (1 ml). The mixture is stirred with cooling for 3 hours and solvent is then removed under reduced pressure while keeping the solution cooled by evaporation. Residual trifluoroacetic acid is removed by co-distillation with benzene in vacuo at room temperature and the residue is triturated once with an ether-pentane mixture and three times with ether yielding the title compound 153 mg., melting point 128°–133° C.; IR (KBr) 1810, 1760 (COOH), 1710 cm$^{-1}$, NMR (CDCl$_3$-CD$_2$OD)δ, 1.47 (S, CH$_3$), 1.63 (S, CH$_3$), 4.15 (S,H$_3$), 5.02 (d, J=4.5 Hz, H$_5$), 5.62 (d, J=4.5 Hz, H$_6$).

Anal. Calc'd for $C_8H_{10}NO_5SBR$: C, 30.78; H, 3.23; N, 4.49; Br, 25.60. Found: C, 31.36; H, 3.13; N, 4.03; Br, 26.21.

What is claimed is:

1. (2S,5R,6S)-6β-Bromo-3,3-dimethyl-7-oxo-4-thia-1-azabicyclo[3.2.0]heptane-2-carboxylic acid, S,S-dioxide, or a physiologically acceptable salt thereof or a readily hydrolyzable ester thereof.

2. A compound in accordance with claim 1, (2S,5R,6S)-6β-bromo-3,3-dimethyl-7-oxo-4-thia-1-azabicyclo[3.2.0]-heptane-2-carboxylic acid, S,S-dioxide.

3. A method of inhibiting the action of the β-lactamase enzyme RTEM in a mammalian host being treated with a β-lactam antibiotic susceptible to degradation by the RTEM enzyme, which comprises administering (2S,5R,6S)-6β-bromo-3,3-dimethyl-7-oxo-4-thia-1-azabicyclo[3.2.0]heptane-2-carboxylic acid, S,S-dioxide, or a physiologically acceptable salt thereof or a readily hydrolyzable ester thereof to the host in conjunction with the antibiotic.

4. A method in accordance with claim 3 wherein the compound is (2S,5R,6S)-6β-bromo-3,3-dimethyl-7-oxo-4-thia-1-azabicyclo[3.2.0]heptane-2-carboxylic acid, S,S-dioxide.

5. A composition comprising a β-lactam antibiotic susceptible to degradation by the β-lactamase enzyme RTEM and (2S,5R,6S)-6β-bromo-3,3-dimethyl-7-oxo-4-thia-1-azabicyclo[3.2.0]heptane-2-carboxylic acid, S,S-dioxide, or a physiologically acceptable salt thereof or a readily hydrolyzable ester thereof.

6. A composition in accordance with claim 5 comprising a β-lactam antibiotic susceptible to degradation by the β-lactamase enzyme and (2S,5R,6S)-6β-bromo-3,3-dimethyl-7-oxo-4-thia-1-azabicyclo[3.2.0]heptane-2-carboxylic acid, S,S-dioxide.

* * * * *

Notice of Adverse Decision in Interference

In Interference No. 100,912, involving Patent No. 4,203,992, E. M. Gordon and W. H. Koster, β-BROMOPENICILLANIC ACID SULFONE, final judgment adverse to the patentees was rendered June 3, 1983, as to claims 1 and 2.
[*Official Gazette November 8, 1983.*]